United States Patent [19]

Rhein et al.

[11] 4,196,129

[45] Apr. 1, 1980

[54] PREPOLYMER DIANHYDRIDES

[75] Inventors: Robert A. Rhein, La Canada; John D. Ingham, La Crescenta, both of Calif.

[73] Assignee: California Institute of Technology, Pasadena, Calif.

[21] Appl. No.: 933,186

[22] Filed: Aug. 14, 1978

Related U.S. Application Data

[63] Continuation of Ser. No. 761,252, Jan. 21, 1977, abandoned.

[51] Int. Cl.$^2$ ............................................. C07D 307/89
[52] U.S. Cl. .................................................. 260/346.3
[58] Field of Search ..................................... 260/346.3

[56] References Cited

U.S. PATENT DOCUMENTS

| | | | |
|---|---|---|---|
| 3,183,248 | 5/1965 | Hirsch et al. | 260/346.3 |
| 3,225,065 | 12/1965 | Hyde | 260/346.3 |
| 3,239,537 | 3/1966 | Steckler et al. | 260/346.3 |
| 3,264,261 | 8/1966 | Stark | 260/346.3 X |
| 3,459,584 | 8/1969 | Caldwell | 260/75 N X |
| 3,919,172 | 11/1975 | Rhein et al. | 260/75 R |

*Primary Examiner*—Richard Raymond
*Attorney, Agent, or Firm*—Marvin E. Jacobs

[57] ABSTRACT

A process for preparing dianhydrides that are miscible with hydroxyl prepolymers at moderate temperatures and can cure hydroxyl prepolymers to elastomers at moderate temperatures is disclosed. The dianhydrides are prepared by solution reaction of a prepolymer diol with excess dianhydride followed by removal of unreacted dianhydride. The prepolymer dianhydrides are miscible with hydroxyl substituted hydrocarbon prepolymers and cure the prepolymers to polyester-linked elastomers.

9 Claims, No Drawings

PREPOLYMER DIANHYDRIDES

ORIGIN OF THE INVENTION

The invention described herein was made in the performance of work under a NASA contract and is subject to the provisions of Section 305 of the National Aeronautics and Space Act of 1958, Public Law 83-568 (72 Stat. 435; 42 USC 2457).

This is a continuation of application Ser. No. 761,252, filed Jan. 21, 1977, now abandoned.

BACKGROUND OF THE INVENTION

1. Field of the Invention

The present invention relates to prepolymer dianhydrides, to their synthesis and to the use thereof in forming polyester-linked elastomers.

2. Description of the Prior Art

Thermally and chemically stable polymers are required for materials applications, particularly highly stable, elastomeric systems for solid-propellant binders in which the initial high temperature required for dissolving the anhydride in the prepolymer would be detrimental. Neat systems, not requiring solvent are desirable from cost and environmental considerations. It is common practice to use diisocyanates in the curing of di- and poly-hydroxy prepolymers to form polyurethanes. The polyurethane curing system is desirable in that the urethane linkage forms without the evolution of by-products. Polyurethanes, however, suffer from the drawback of thermal instability at elevated temperatures.

The ester linkage is believed to possess considerably superior thermal stability compared to the urethane linkage. However, polyesters are generally prepared by the alcohol-carboxylic acid reaction, wherein water is emitted as a by-product, and elevated temperatures, around 200° C., are required for this reaction. However, the anhydride-alcohol reaction produces no by-products.

The curing of hydroxy-terminated prepolymers by the use of dianhydrides has been described, either in the absence of solvent (U.S. Pat. No. 3,919,172) or in solution (U.S. Pat. No. 3,459,584). However, the latter reference is not relevant to solventless (neat) systems, and although solvents were not used in the first mentioned patent, it was found necessary to heat the dianhydride (either pyromellitic dianhydride or tetrahydrofuran-tetracarboxylic dianhydride)-prepolymer diol mixture to temperatures exceeding 200° C. to obtain a clear prepolymers-dianhydride solution before curing could proceed.

Pyromellitic dianhydride (PMDA) derivatives are disclosed in British Pat. No. 886,601 by the reaction of 2:1 mole ratio of PMDA with various diols in certain solvents. The reaction products, still in the solvent, were used to cure with diepoxides. In the examples of the British patent, product analyses were not given, nor was the product used to cure prepolymer diols. Since the solvents utilized had a low solubility for PMDA, most likely the product was a polyester dianhydride, which in turn acted as solvent for unreacted PMDA. Such a mixture would not likely be useful for curing prepolymer diols, as the unreacted PMDA, although possibly soluble in the polyester dianhydride, would likely precipitate out upon mixing with prepolymer diol. It is believed that the PMDA derivatives are most likely mixtures of unreacted dianhydride plus polymers for the reason that the solvents disclosed there have a rather small solubility for PMDA and high solubility for diol. This fact alone suggests the formation of a diol-dianhydride polyester copolymer.

The prepolymer dianhydrides of the British patent have only been shown to cure epoxies. In actuality, the pendant carboxylic acid of the PMDA derivatives is sufficient to cure the epoxies.

Consider this argument schematically:

Let a dihydroxy prepolymer or compound be represented as HO—P—OH and let a dianhydride (PMDA, THFTDA, etc.) as

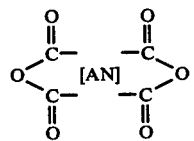

In the process of the British patent the solvent has a low solubility of dianhydride and good solubility for diol. What most likely happens is this:

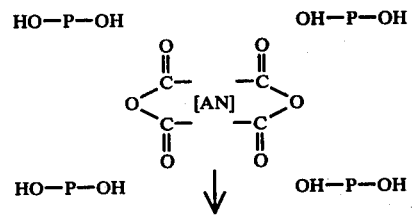

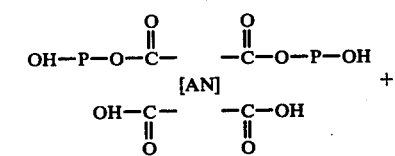

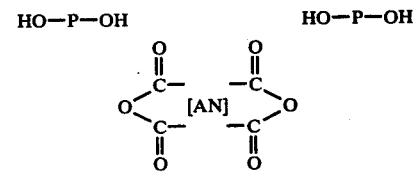

As more anhydride enters the solution, we get this:

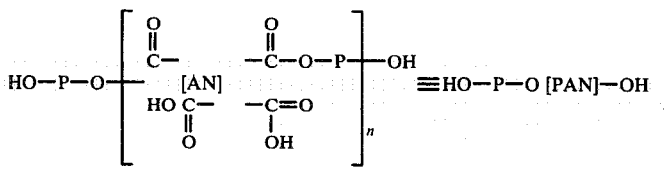

This would continue until the HO—P—OH is used up; then the terminal hydroxyls would react with dianhydride, the mixture composition being most likely:

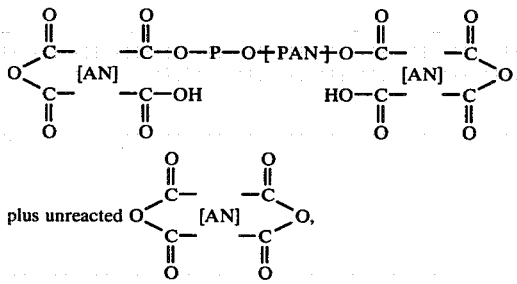

which may be soluble in the above polymer to make the homogeneous solutions claimed. However, if the solvent were removed, the products may well be hard, high-melting materials possessing no real advantage over PMDA or THFTDA in the curing of hydroxyl polymers.

SUMMARY OF THE INVENTION

Prepolymer dianhydrides have been prepared in accordance with this invention that are miscible with and cure hydroxyl prepolymers at moderate temperature to form polyester linked elastomers. Processing is similar to polyurethane system but thermal stability is significantly increased as is hydrolytic stability. The cure is effected without evolution of by-products.

The prepolymer dianhydrides of the invention are prepared by the solution reaction of prepolymer diols with a great excess of dianhydride, preferably the molar ratio of dianhydride to diol being at least 5:1, preferably at least 10:1 to 25:1. After reaction unreacted dianhydride is removed. The reaction scheme follows:

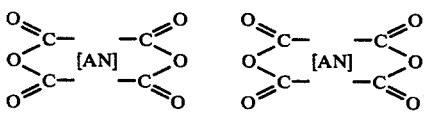

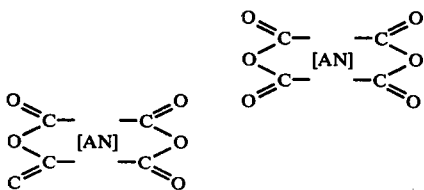

Producing

-continued

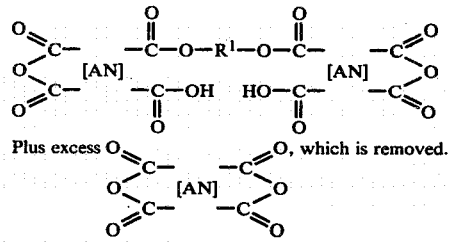

Polymerization products are at a minimum in the process of the invention. Furthermore softening temperature of the prepolymer dianhydride can be controlled by selection of prepolymer diol. The process of the invention is based on the presence of a large excess of dianhydride. The large excess is made possible by use of highly polar aprotic solvents in which the dianhydrides have substantial solubility such as dimethylacetamide (DMAC), dimethylformamide (DMF), dimethylsulfoxide, sulfolane or N-methylpyrrolidone or the like. The dianhydrides useful in this invention are dianhydrides of the formula:

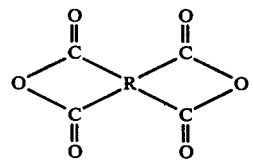

where R is a tetravalent organic group containing 4 to about 40 carbon atoms, preferably 6–20 carbon atoms and may contain other atoms such as nitrogen or oxygen. Suitable dianhydrides are tetrahydrofuran tetracarboxylic dianhydride (THFTDA), pyromellitic dianhydride (PMDA) or benzophenone tetracarboxylic dianhydride. Other dianhydrides are disclosed in U.S. Pat. Nos. 3,182,073, 3,182,074 and 3,183,248. The dianhydrides when in the prepolymer adduct form of this invention provide effective chain extension of prepolymer polyols.

The polyols are selected from compounds of the formula:

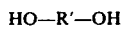

wherein R' is the residue of an organic molecule having a molecular weight from 300 to 8,000, preferably 400 to 5,000. The functionality of the prepolymer is advantageously from 1.7 to 3.0, preferably from 1.9 to 2.5. R' may be a polyester, polyether, saturated hydrocarbons or copolymers or a dimerized fatty acid and derivatives thereof.

Polybutadiene polymer may be hydrogenated to provide increased stability in high temperature environments or the prepolymer may be formed from saturated aliphatic hydrocarbon prepolymers such as hydroxyl terminated polypropylenes, polybutylenes or polyisobutylenes.

The poly(ether glycol) useful in this invention typically contains from 2 to 4 carbon atoms between the ether groups and contains sufficient repeating units to provide a poly(ether glycol) having a molecular weight of about 400 to about 8,000. Typical poly(ether glycols) useful in this invention are: polyethylene glycol, polypropylene glycol, poly(1,3-propylene glycol), poly(1,2-butylene glycol) and poly(1,1-butylene glycol).

Metal acetyl acetonates such as iron, copper or nickel acetyl acetonates are effective catalysts for the desired adduct reaction. Ferric acetyl acetonate is the most effective catalyst providing adducts at the lowest temperatures and in the shortest reaction periods. The mole ratio of catalyst to anhydride is suitably from 0.001 to 0.5, preferably from 0.02 to 0.2.

The prepolymer dianhydride is synthesized by combining the dianhydride and prepolymer diol and forming a solution in a comutual highly polar solvent. Catalyst may be added to increase reaction rate. The solution may be heated to a low temperature of 50° C. to 150° C., preferably 70° C. to 110° C. to aid solution and increase reaction rate. After a suitable reaction period, the solvent is removed by evaporation and the prepolymer dianhydride recovered by solvent extraction and precipitation.

The prepolymer dianhydride readily forms polyester linked elastomers by reaction at low temperatures with prepolymer diols such as those described above or other materials such as castor oil or unsaturated prepolymers such as polybutadiene diols. The diols utilized in the Examples are ARCO-Poly B-D R-45 which is an hydroxy-terminated polybutadiene containing 0.684 eq/kg of hydroxyl and DB oil which is a refined castor oil containing 2.93 eq/kg of hydroxyl.

These and other features and attendant advantages of the invention will become better understood by reference to the following detailed description.

DESCRIPTION OF THE PREFERRED EMBODIMENTS

Example I 11.2 Grams of Emery 9360A (the bis-hydroxyethyl derivative of dimer acid), with hydroxyl content 2.51 eq/kg, was added to a 111 ml. round-bottom flask. 23.6 Grams of THFTDA was added to make a mole ratio of anhydride/hydroxyl=8.0. Then 0.1 gm. of ferric acetylacetonate (FeAA) was added, and 51 ml. DMAC poured in. The mixture was heated, with stirring, to 70° C. to form a homogeneous solution, and was kept at 70° C. for 14 hours. The mixture was transferred to a 250 ml. flask, 40 ml. tetralin added, and the DMAC vacuum-stripped at 70° C. from the mixture, leaving a soft solid residue consisting of tetralin, reaction product, and excess THFTDA. 50 ml. benzene and 50 ml. hexane was added, the mixture beaten in a Waring blender, and the solid was allowed to settle. The solution was poured into another vessel, and solvent stripped at 70° C. Then 40 ml. benzene, 40 ml. heptane, and 100 ml. benzene was added to the mixture and stirred, whereupon solid was again observed. The solid, presumably unreacted THFTDA, was allowed to settle. The clear solution was removed and vacuum-evaporated at 70° C. to form a brown, transparent product. Analysis of the product indicated the following (in equivalent/kg): hydroxyl, 0.4; anhydride, 2.09; carboxylic acid 1.12. Gel permeation chromatography indicated, discounting products of molecular weight less than 470, a number-average molecular weight (Mn) of the product of 1450. This data can be reconciled to a model that indicates the product to be a polymer of degree of polymerization 1.31, containing 6.56% (molar) unreacted THFTDA, and 15.9 percent (molar) unreacted hydroxyl.

To indicate the application of this product in the curing of hydroxyl prepolymers, 1.7 gm. was added to 4.1 grams of ARCO POLY B-D, R45, containing 0.684 eq/kg of hydroxyl. A fluid mixture of the two materials was prepared by stirring at 100° C.; upon mixing, the solution was kept at 70° C. over a weekend. The product was a gelled elastomer.

Example 2

11.4 Grams of Emery 9360A was mixed with 25.0 grams of pyromellitic dianhydride and 0.1 gm. FeAA and 200 ml. of DMAC was added. The mixture became a clear solution at 110° C. The mixture was kept at 70° C. for 14 hours and cooled to ambient, whereupon considerable unreacted PMDA precipitated. The mixture was processed as in example 1, yielding 15.7 grams of a product containing (eg./kg): Hydroxyl, 0.3; anhydride, 0.39, carboxyl, 1.37, and Mn 2750. This data is consistent with the product of degree of polymerization (DP)2.52, containing 11.9% (molar) unreacted hydroxyl but with 35.9 (molar)% of the anhydride expected, the remainder having hydrolyzed to carboxylic acid.

2.0 Grams of product were mixed with 4.7 grams of ARCO R45 in one sample and 1.5 grams were mixed with 0.8 grams of refined castor oil (DB Oil, Baker Castor Oil Co., hydroxyl 2.93 eq/kg) in another sample. These did not cure at 70° C. for 42 hr., but both produced elastomers upon a post-cure at 120° C. for 16 hours.

Example 3

Dimer acid (Empol 1010, Emery Corp.) was reduced with sodium aluminum diethyl dihydride to the extent of 2:1 mole ratio in toluene according to the procedure disclosed by the inventors in Polymer 16, 799–804 (Nov. 1975). The product contained 3.60 mg/gm hydroxyl, and is referred to here as 7185A.

10.8 Grams of 7185A, 33.0 grams of THFTDA (anhydride/hydroxyl=8:1), and 0.1 gm. FeAA were reacted and processed as described in example 1, producing 19.6 grams of a product analyzed to contain (eg/kg): hydroxyl, 0.92; anhydride, 3.08; carboxylic acid, 2.08; also by GPC, Mn 1230. This data is consistent with a product of DP 1.39, containing 13% (molar) unreacted dianhydride and 25.6% (molar) unreacted hydroxyl. 2.1 Grams of product were mixed with 6.3 grams of ARCO R-45 in one experiment, and 0.5 grams of product were mixed with DB Oil in another experiment; both experiments were kept at 70° C. for 42 hours. In both cases the mixtures cured to elastomers.

Example 4

21.8 Grams of PPG2025 (polypropylene oxide, OH 1.0 meq/gm.) were reacted with 18.5 gm. THFTDA (mole ratio anhydride/hydroxyl=8:1) and 0.1 gm FeAA as in example 1. 29.0 gm. of product resulted, which upon analysis indicated no hydroxyl, 0.78 meg/gm. anhydride, 1.58 meg/gm. carboxyl, and Mn 2050. This is consistent with essentially no polymerization of the product, 3.53% (mole) unreacted anhydride but 67.4% (molar) of the anhydride not hydrolyzed, the remainder having hydrolyzed to carboxylic acid.

3.8 gm. of this product was mixed with 1.6 grams of a mixture of 4.47% trimethylolpropane in PPG 2025 (this mixture contained 1.914 meq/gm hydroxyl). This combined mixture did not cure at 70° C., 42 hours, but did cure upon post-treatment at 120° C., 16 hours.

Example 5

10.7 gm of Emery 9360A was mixed with 17.1 gm of THFTDA (mole ratio anhydride/hydroxyl=6.1) and 0.1 gm FeAA and processed as in example 1, yielding 14.8 gm. of product. Analysis indicated (meq/gm) hydroxyl, 0.48; anhydride, 1.62; carboxylic acid, 1.30 Mn=1790. The analysis is consistent with DP=1.61, 19.1% (mole) unreacted hydroxyl, 27% free dianhydride, with 45.7% of the anhydride not hydrolyzed. In two curing experiments, one sample consisted of 1.4 gm product with 3.4 gm. ARCO R-45; the other consisted of 0.4 gm. product and 0.2 gm DB oil. Satisfactory cures to elastomers were obtained in both cases at 70° C., 42 hours.

Example 6

11.6 Grams of Emery 9360A, 12.4 grams of THFTDA (anhydride/hydroxyl=2.0) and 0.1 gm FeAA were processed as in example 1 to yield 18.2 grams of product. Analyses indicated (meq/gm) hydroxyl, 0.78; anhydride, 1.08; and carboxylic acid, 1.66; Mn=1932. This data is consistent with DP=1.77, 31.1% (mole) unreacted hydroxyl, and 2.3% free anhydride; in this example, no anhydride hydrolysis was determined.

1.4 gm product was mixed with 3.4 gm. ARCO R-45 in one experiment and 0.5 gm product was mixed with 0.3 gm. DB oil in another and both were held at 70° C. for 42 hours. Incomplete cure was observed in the first case, satisfactory cure in the second.

Example 7

20.8 gm of Emery 9360A 11.6 gm THFTDA (anhydride/hydroxyl=2.1), 0.1 gm FeAA, and 30 ml. DMAC were stirred at 70° C. until the mixture became a homogenous solution. The solution was kept at 70° C. for 16 hours.

The DMAC was removed by vacuum evaporation leaving a transparent product. Analysis indicated (eq/mg) no hydroxyl, anhydride, 0.34, carboxylic acid 3.56, and Mn-2256. This data is consistent with DP-2.03, 3.6% (mole) unreacted dianhydride, but with all but 27.7% (mole) of the anhydride having hydrolyzed. When 2.3 gm of product and 5.5 gm ARCO R-45 were mixed and held at 70° C. over a weekend, a soft, but gelled, elastomer resulted.

Example 8

23.8 gms Emery 9360A, 12.3 gm THFTDA (anhydride/hydroxyl=2.1), 0.1 gm. FeAA, and 40 ml. N-methylpyrrolidone were mixed to a homogenous solution at 70° C. for 18.5 hours. The solvent was removed by vacuum evaporation leaving a transparent product. Analysis indicated (eq/kg) hydroxyl, 0.74; anhydride, 0.57; carboxylic acid, 2.5; and Mn 1900. This data is consistent with DP=1.77, 45.2% (mole) unreacted hydroxyl, 9.4% (mole) free anhydride, but only 32% (mole) of the anhydride not hydrolyzed. In two curing experiments, 2.0 gms. product were mixed with 4.8 gm. ARCO R45 in one and 3.2 gm. product were mixed with 1.8 gm. DB-oil in the other; both held at 70° C. for 42 hrs; both cured to somewhat sticky elasomers.

Example 9

4.9 gm. Emery 9260A, 2.6 gm THFTDA (anhydride/hydroxyl=2.1), 0.1 gm. FeAA, and 20 ml. dimethylformamide (DMF) were mixed together at 70° C. The THFTDA dissolved, but the diol did not seem to dissolve fully. The cloudy mixture was stirred at 70° C. for 17 hours. The DMF was then removed by vacuum evaporation, leaving an inhomogeneous-appearing product. Analysis indicated (eq/kg): hydroxyl, 0.66; anhydride, 0.54; carboxyl, 4.13; and Mn 1940. This data is consistent with DP=1.80, 40.3% (mole) unreacted hydroxyl, 1.1% free anhydride and 59.0% of anhydride not hydrolyzed. When 1.1 gm of product was mixed with 2.6 gm ARCO R45 and the mixture held at 70° C. over a weekend, the resulting product was a soft, sticky elastomer, suggesting incomplete cure.

In conclusion, both a novel process for preparing prepolymer dianhydrides, as well as the prepolymer dianhydrides themselves, have been disclosed. The prepolymer dianhydrides have been found to mix easily with hydroxyl prepolymers and cure these hydroxy prepolymers by polyester linkages to elastomers. The process utilizes a highly polar solvent that completely dissolves the dianhydride (THFTDA or PMDA) as well as the diol, uses FeAA as catalyst, and is carried out at a temperature<100° C., preferably 70° C. to prevent the hydroxyl-carboxylic acid esterification reaction. In addition, the process consists of using substantial excess of dianhydride to prevent substantial copolymerization of diol and dianhydride; excess dianhydride following the reaction is then removed. The dianhydride prepared from the dihydroxy derivative of dimer acid has a low softening temperature and is particularly suitable for the curing of hydroxy-prepolymers.

It is to be realized that only preferred embodiments of the invention have been described and that numerous substitutions, modifications and alterations are permissible without departing from the spirit and scope of the invention as defined in the following claims.

What is claimed is:

1. A process of preparing a prepolymer-dianhydride adduct comprising the steps of:
   forming a solution of a prepolymer diol selected from compounds of the formula:

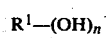

where $R^1$ is the residue of an organic molecule having a molecular weight from 300 to 8,000 and n is a number from 1.7 to 3.0; and a dianhydride selected from compounds of the formula:

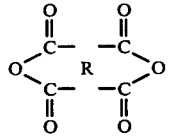

where R is a tetravalent organic group containing 4 to 40 carbon atoms in a highly polar comutual solvent selected from dimethyl acetamide, dimethylformamide, dimethylsulfoxide, sulfolane or N-methylpyrrolidone in which the molar ratio of dianhydride to diol is at least 5:1;

reacting the diol and dianhydride to form an adduct of the formula:

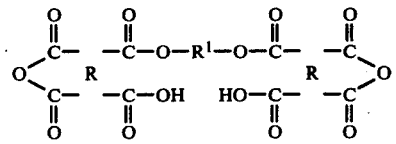

and recovering the adduct from the solution.

2. A process according to claim 1 in which the ratio of anhydride to prepolymer diol is from 10:1 to 25:1.

3. A process according to claim 1 in which the dianhydride is selected from tetrahydrofuran tetracarboxylic dianhydride, pyromellitic dianhydride, or benzophenone tetracarboxylic dianhydride.

4. A process according to claim 1 in which the molecular weight is from 400 to 5,000 and n is a number from 1.9 to 2.5.

5. A process according to claim 1 in which R' is selected from polyester, polyether, saturated aliphatic hydrocarbon or dimer fatty acid.

6. A process according to claim 1 further including the step of forming a polyester linked elastomer by reacting the separated adduct with prepolymer polyol.

7. A process according to claim 1 in which the solution further includes a metal acetylacetonate catalyst and the catalyst to anhydride mole ratio is from 0.001 to 0.5.

8. A process according to claim 7 in which the catalyst to anhydride ratio is from 0.02 to 0.2.

9. A process according to claim 7 in which the adduct reaction is conducted at a temperature less than 100° C.

* * * * *